United States Patent
Johansen et al.

(10) Patent No.: US 6,387,352 B1
(45) Date of Patent: *May 14, 2002

(54) MOUTHWASH COMPOSITIONS

(75) Inventors: Erling Johansen, Needham, MA (US); Thor Olsen, Rochester, NY (US); Athena Papas, Weston, MA (US)

(73) Assignee: Erling Johansen, Needham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/350,965

(22) Filed: Jul. 9, 1999

Related U.S. Application Data

(63) Continuation of application No. 08/933,481, filed on Sep. 18, 1997, now Pat. No. 5,993,785.
(60) Provisional application No. 60/026,578, filed on Sep. 18, 1996.

(30) Foreign Application Priority Data

Sep. 18, 1996 (GB) ............................... 9619464

(51) Int. Cl.⁷ .............................. A61K 7/16; A61K 7/18
(52) U.S. Cl. .............................. 424/49; 424/52; 424/57
(58) Field of Search ...................... 424/49–58

(56) References Cited

U.S. PATENT DOCUMENTS

| | | | |
|---|---|---|---|
| 3,679,360 A | 7/1972 | Rubin et al. | 23/109 |
| 4,048,300 A | 9/1977 | Tomlinson et al. | 424/52 |
| 4,080,440 A | 3/1978 | DiGuilio et al. | 424/57 |
| 4,083,955 A | 4/1978 | Grabenstetter et al. | 424/49 |
| 4,097,588 A | 6/1978 | Levine | 424/52 |
| 4,097,935 A | 7/1978 | Jarcho | 3/1.9 |
| 4,108,980 A | 8/1978 | Duff | 424/52 |
| 4,177,258 A | 12/1979 | Gaffar et al. | 424/52 |
| 4,183,915 A | 1/1980 | Gaffar et al. | 424/52 |
| 4,348,381 A | 9/1982 | Gaffar et al. | 424/52 |
| 4,397,837 A | 8/1983 | Raaf et al. | 424/57 |
| 4,532,124 A | 7/1985 | Pearce | 424/57 |
| 4,606,912 A | 8/1986 | Rudy et al. | 424/57 |
| 5,037,639 A | 8/1991 | Tung | 424/57 |
| 5,268,167 A | 12/1993 | Tung | 424/57 |
| 5,427,768 A | 6/1995 | Tung | 424/57 |
| 5,437,857 A | 8/1995 | Tung | 424/57 |
| 5,460,803 A | 10/1995 | Tung | 424/57 |
| 5,562,895 A | 10/1996 | Tung | 424/57 |
| 5,571,502 A | 11/1996 | Winston et al. | 424/57 |
| 5,603,922 A | 2/1997 | Winston et al. | 424/57 |
| 5,605,675 A | 2/1997 | Usen et al. | 424/57 |
| 5,614,175 A | 3/1997 | Rudy et al. | 424/57 |
| 5,658,554 A | 8/1997 | Fischer et al. | 424/57 |

FOREIGN PATENT DOCUMENTS

| | | |
|---|---|---|
| GB | 1090340 | 11/1967 |
| GB | 1408922 | 10/1975 |
| GB | 1509977 | 5/1978 |

OTHER PUBLICATIONS

Koulorides, Experimental Changes of Enamel Mineral Density, Harris: Art and Science of Dental Caries Research, 355–378 (Acad. Press, NY 1968).
Johansen, E., et al., *Gerodontics*, 3, 47–50 (1987).
Office of Cancer Communications, Research Report on Leukemia, National Cancer Institute, NIH Publication No. 88–329 (1988).
Epstein, J.B., *NCI Monogr.,* 9, 73–85 (1990).

*Primary Examiner*—Shep K. Rose
(74) *Attorney, Agent, or Firm*—Synnestvedt & Lechner LLP

(57) ABSTRACT

Aqueous solutions are disclosed which are supersaturated with respect to calcium phosphate(s) and which further comprise a stabilising agent in an amount sufficient to enable the calcium ions and phosphate ions to remain in supersaturated solution so that it may be used as a dental rinse or mouthwash. Such solutions are suitable for treating patients having dental caries or other conditions of the oral cavity.

64 Claims, No Drawings

MOUTHWASH COMPOSITIONS

RELATED APPLICATIONS

This application is a continuation of U.S. application Ser. No. 08/933,481, filed Sep. 18, 1997 now U.S. Pat. No. 5,993,785, which claims the benefit of U.S. Provisional Application No. 60/026,578, filed Sep. 18, 1996.

FIELD OF THE INVENTION

The present invention relates to calcium- and phosphate-containing compositions for use as mouthwashes or dental rinses. In particular, it relates to solutions supersaturated with calcium and phosphate, their preparation and use.

BACKGROUND OF THE INVENTION

By "supersaturated" with calcium and phosphate is herein meant that higher concentrations of calcium ions and orthophosphate ions are present in the solution than would be present in a saturated solution of those ions.

British patent specification no. GB 1 090 340, published in 1967, discloses compositions for rehardening dental enamel comprising fluoride, calcium, phosphate and sodium chloride which yield, on contact with saliva, supersaturated solutions to form hydroxyapatite. Because saliva is required to form the supersaturated solution, the preferred compositions are in the form of confectionery such as chewing gum. However, it is known that, under most circumstances, saliva is already supersaturated with calcium and phosphate. No disclosure is given of how to make a supersaturated solution ab initio which can then be used effectively in the form of a mouthwash or dental rinse. Furthermore, no mention is made of the possibility of excluding fluoride; or of the formation of octacalcium phosphate by the supersaturated solution in the saliva. In any case, in the absence of or where there is a significantly reduced mount of saliva, these compositions would not work as described.

A supersaturated solution is disclosed in U.S. Pat. No. 5,427,768 which is supersaturated with calcium phosphate and carbon dioxide and used to deposit apatite on the teeth. However, in this case, the supersaturation is caused by release of carbon dioxide, and carbonate is absorbed by the teeth which results in a deposited mineral phase with decreased resistance to dental caries.

British patent specification no. GB 1 408 922, published in 1975, discloses an oral treatment pack which comprises two phases for sequential application to teeth, the isolated phases comprising calcium (50 to 35000 ppm) and phosphate (50 to 40000 ppm) compounds, respectively. However, there is no disclosure or teaching regarding how to make a single phase, supersaturated solution within these concentration ranges which cover four orders of magnitude. Indeed, Example 3 thereof teaches two phases which, if mixed, would result in immediate precipitation of calcium phosphates.

A further solution containing calcium and phosphate is disclosed in British patent specification no. GB 1 509 977, published in 1978. This solution comprises one component containing calcium ions (at least 30 ppm) and another component containing at least 100 ppm fluoride, one or both components also containing phosphate ions (at least 0.1M) such that on mixing the components hydroxyapatite can be deposited therefrom on teeth. However, such solutions are not stably supersaturated (indeed, this patent teaches that the phosphate ions can be incorporated only in the solution containing calcium ions (at low concentration) which would not allow for the preparation of a stable, non-precipitating, supersaturated solution), and contains greater fluoride than considered to be clinically safe if accidentally swallowed. Again, no reference is made to producing octacalcium phosphate deposits.

BRIEF DESCRIPTION OF THE INVENTION

On the other hand, the present invention relates to an aqueous solution suitable for use as a dental rinse or mouthwash, which solution is supersaturated with respect to calcium phosphate(s) and which solution further comprises a stabilising agent such as sodium chloride (NaCl).

Although, as previously mentioned, it is known that, normally, saliva is supersaturated with respect to calcium and phosphates, the supersaturated solutions of the present invention contain significantly higher concentrations of those ions. Since the degree of supersaturation of saliva is variable from individual to individual, it is not possible to state definitively how much more supersaturated are the solutions of the present invention, but they may in many cases contain of the order of from 5 to 10 times the concentrations of calcium and phosphate ions than normal saliva.

The present inventors have disclosed (Gerodontics 3, 47–50 (1987)) the remineralisation of carious lesions in elderly patients using an experimental regimen which included mouthwashing with a solution comprising 5 mM Ca, 3 mM $PO_4$ and 0.25 mM (5 ppm) fluoride, stabilised by NaCl, at pH 7.0. No other uses of the solution were mentioned and no details concerning the preparation of the solution were given other than that "two stock solutions were stored separately and mixed in proper volumes immediately before use".

The supersaturated solutions of the present invention are required to be prepared just prior to use due to the degree of supersaturation thereof and the risk of precipitation of calcium phosphate (mineral) therefrom.

DETAILED DESCRIPTION OF THE INVENTION

Accordingly, the present invention provides a formulation suitable for use as a dental rinse or mouthwash, which formulation comprises:

(a) a calcium component (calcium stock solution) which itself comprises an aqueous solution of calcium ions and stabiliser; and, associated therewith but separate therefrom, (b) a phosphate component (phosphate stock solution) which itself comprises an aqueous solution of phosphate ions and stabiliser wherein the calcium and phosphate are present in amounts sufficient to form, on mixing, a supersaturated solution thereof, as described hereinbelow.

The present invention therefore specifically provides a multi-component formulation suitable for use as a dental rinse or mouthwash, which formulation comprises:

(a) a calcium component (calcium stock solution) which itself comprises an aqueous solution of calcium ions having a concentration in the range of from about 4 to about 80 mM and from about 40 to about 400 mM stabiliser; and, associated therewith but separate therefrom, (b) a phospate component (phosphate stock solution) which itself comprises an aqueous solution of (ortho) phosphate ions having a concentration in the range of from about 1 to about 64 mM and from about 40 to about 400 mM stabiliser
whereby, on mixing, the components form a solution supersaturated with respect to calcium phosphate(s).

The supersaturated solutions of the present invention remain stable at least for the length of time and under normal conditions of their use. By this is meant that the supersaturated solution remains substantially supersaturated with respect to calcium and orthophosphate ions for the normal time the solution is rinsed or washed around the oral cavity. After this time, the solution may begin to contain some precipitate of calcium phosphates which would reduce its therapeutic effectiveness. Therefore, conveniently, the solution may remain supersaturated in the oral cavity for up to about five minutes, especially up to 2–3 minutes and necessarily up to about 1 minute, all measurements therefore taken at body temperature. It will be understood that, at lower temperatures such as room or ambient temperature, the supersaturated solution will remain so for significantly longer periods such as of the order of up to 2 hours, especially up to 1 hour and necessarily for the length of time taken to use the supersaturated solution just mixed as a dental rinse or mouthwash which may be in the range of from about 3 minutes to about 15 minutes.

Preferably components (a) and (b) do not, respectively, contain any phosphate or calcium, although minor amounts (up to 10–20% either way—less at higher pH and vice versa) could be tolerated.

Preferably, the supersaturated solution has a pH of from about 5 to about 8.0, more preferably of from about 6 to about 7.5, such as about 6.5 to about 7.5; especially preferred is when the pH is about neutral such as 7.0±0.2. The pH of each stock solution component may vary widely: for component (a), it is in the range 1 to 12.5, preferably 3.5 to 8, more preferably 4 to 7.5; for component (b), it is in the range 2 to 13, preferably 4 to 8.5, more preferably 5 to 7.5. The pHs of components (a) and (b) in the case where the pH of the supersaturated solution is to be around neutral are preferably around 4 to 7.5, more preferably 4 to 6, especially around 4; and 5 to 7.5, preferably 7 to 7.3, more preferably around 7.2, respectively.

Preferably, the concentration of calcium ions (total $Ca^{2+}$ i.e. free and complexed) in the supersaturated solution is in the range of from 2 to about 40 mM, such as 2 to about 21 mM, more preferably in the range of from 2.5 to 16 mM. At around neutral pH, the concentration of calcium ions in the supersaturated solution is suitably in the range of from 2.5 to about 10 mM, preferably 3 to 5 mM, for example, about 3.87, 4.5 or 5 mM calcium ions. Especially suitable is when the concentration of calcium ions is around 4.5 to 5 mM, for example, 4.74 mM particularly to promote formation of octacalcium phosphate.

Component (a) most preferably contains calcium as calcium chloride. Other sources of calcium which have been used in mouthwashes include calcium nitrate, calcium hydroxide or calcium carbonate, optionally including a minor amount of calcium phosphate, dissolved in an acid such as HCl, Preferred sources of calcium are calcium nitrate and calcium hydroxide, but calcium chloride is most preferred. The concentration of calcium ions in component (a) is conveniently double that In the supersaturated solution and therefore suitably In the range of from about 4 to about 80 mM. Preferably, the range is from about 4 to about 40 mM, more preferably 5 to 32 mM, especially 5 to 20 mM, and more especially around 10 mM, for example 9.47 mM.

Preferably, the concentration of phosphate ions (total (ortho)phosphate) in the supersaturated solution is in the range of from about 0.5 to about 32 mM, preferably about 1 to 20 mM such as 1.5 to about 10 mM. At around neutral pH, the concentration of phosphate is suitably in the range of from about 2 to about 6 mM, preferably 2 to 4 mM, for example, about 2, 3, 3.4 or 3.87 mM. Especially suitable is when the concentration of phosphate ions is around 2.7 to 3.4 mM, for example, 2.96 mM to promote formation of octacalcium phosphate.

Component (b) preferably contains phosphate as a mixture of monobasic phosphate with dibasic phosphate. To comply with the much preferred pH of the supersaturated solution (pH=7.0±0.2), the ratio of mono:dibasic phosphate is in the order of about 1:2–1:8, preferably 1:2.5–1:3.5, such as about 1:3. At the higher concentrations of calcium and phosphate in the stock solutions, the amount of dibasic phosphate would increase relative to monobasic phosphate.

Alternatively, a pH adjuster such as alkalimetal hydroxide or ammonium hydroxide or tribasic phosphate such as a tri(alkalimetal) phosphate could be used to deliver the preferred pH of the supersaturated solution. Since the quantity of hydroxide is more difficult to measure than that of dibasic phosphate, It is preferred to use monobasic phosphates and dibasic phosphates. Another alternative is to use a combination of phosphoric acid with a dibasic or tribasic such as tri(alkalimetal) phosphate. Preferred alkali metals in this context are sodium and potassium, especially sodium.

The concentration of phosphates in component (b) is conveniently double that for the supersaturated solution and therefore is preferably in the range of from about 1 to about 64 mM, preferably from about 2 to about 40 mM, such as about 3 to about 20 mM, preferably at the preferred pH ranges about 4 to about 12 mM, more preferably about 4 to about 8 mM, for example, 5.92 mM. The phosphates are preferably incorporated in the form of their sodium, potassium or ammonium salts; more preferably, sodium salts are employed. However, in cases where hypertensive effects of sodium ions are of concern, mono- and di-potassium phosphates may be used.

To permit use of high concentrations of calcium and phosphate, the solutions incorporate a stabilizing agent which comprises one or more salts of innocuous ions such as the cations $Na^+$, $K^+$, $NH_4^+$, $Mg^{++}$ and $Sr^{++}$, and anions $Cl^-$, $CO_3^-$, $HCO_3^-$, $SO_4^-$ and $NO_5^-$, but preferably comprises primarily sodium chloride or potassium chloride, and most preferably sodium chloride, except when the solution is for use by hypertensive patients.

When present as the stabiliser, the concentration of sodium chloride in the supersaturated solution preferably ranges from about 40 mM to about 400 mM, more preferably 80 mM to 200 mM, such as around 100 mM. The concentration of NaCl is not very dependent upon pH but it is important not to reduce its concentration substantially below this range or precipitation, rather than a supersaturated solution, will result. Alternative stabilising agents may be used provided they are physiologically acceptable, such as other alkali metal halides such as KCl or other compounds having equivalent effect such as ammonium chloride; but NaCl is much preferred The lower end of the range of stabiliser concentration is employed when lower ends of the ranges of calcium and phosphate concentrations are employed, and ice versa.

The amount of stabiliser in each component is sufficient to enable the calcium and phosphate ions to remain in supersaturated solution once components (a) and (b) are mixed. The concentration of sodium chloride (when used in both components) in each component is equivalent to that in the supersaturated solution and therefore preferably ranges from about 40 mM to about 400 mM, more preferably 80 mM to 200 mM, such as around 100 mM. Incorporation of a stabiliser in both components (a) and (b) allows the use of higher-than-otherwise concentrations of calcium and phosphate ions due to the effect of the stabiliser on total ionic strength and thus on the activities of the calcium and phosphate ions ('salt effect'). Increasing the quantity of stabiliser present increases the possible amounts of calcium and phosphate ions which can be present without rapid or spontaneous precipitation. However, due to the intended use of the supersaturated solution as a mouthwash, the amount of NaCl present in each component (a) and (b) should be limited so that the supersaturated solution is approximately isotonic, to avoid irritation or pain in the oral cavity. Preferably, the ratio of NaCl present in component (a):component (b) is in the order of about 1:1.

Since some of the sodium and chloride ions in the stock or supersaturated solutions may arise from: ingredients other than sodium chloride, as guidance, the following amounts of each ion may be present in the supersaturated solution, chloride may be present in the range of from 0 to about 0.5M, preferably 0.05 to 0.3M, more preferably 0.05 to 0.25M, for example 0.103M; and sodium,(ion) may be present in a similar concentration independently selected from similar ranges, for example 0.107M. In the calcium or phosphate stock solutions (a) or (b), both ions may again be present in similar concentrations in the range of from 0 to about 1M, preferably from 0 to about 0.6M, more preferably 0 to 0.5M, for example, 0.098M ($Na^+$) and 0.117M ($Cl^-$) in the calcium stock solution (a); and, for example, 0.108M ($Na^+$) and 0.098M ($Cl^-$) in the phosphate stock solution (b), Preferably, the ratio of concentrations of calcium to phosphate in the supersaturated solution corresponds to 1:1 to 5:3; more preferably 4:3 to 5:3 to increase the amount of octacalcium phosphate formed.

The supersaturated solution may also contain other physiologically-acceptable ions. However, due to the formation of a supersaturated solution (as hereinabove described) on mixing, we have surprisingly found that it is not necessary to incorporate fluoride for clinical effectiveness. But if it should be desired to include fluoride, it is present in the supersaturated solution in the range of from 0 to about 10 mM, preferably 0 to 2.5 mM such as 0 to 0.5 mM, for example 0.25 mM. This preferred range corresponds to a maximum concentration of around 50 ppm, preferably around 5–10 ppm. Inclusion of fluoride in the supersaturated solutions of this invention does not require adjustment of calcium and for phosphate Ion concentrations; in these supersaturated solutions, fluoride and calcium fluoride complexes are formed. In prior art solutions, monofluorophosphate is usually formed.

Where fluoride is to be present, it is preferably added to component (b). It should not all be added to component (a). Therefore, about twice the concentration of fluoride must be present in the phosphate concentrate (b) as specified above for the supersaturated solution. The fact that the supersaturated solutions of the present invention are clinically effective in remineralising teeth in the absence of fluoride is surprising, especially given the emphasis on including fluoride in remineralising solutions in the prior art. For example, Koulorides in Experimental Changes of Enamel Mineral Density [in Harris: Art and Science of Dental Caries Research, pp 365–378 (Acad. Press, N.Y., 1968)] showed that, in enamel re-hardening experiments using calcium/phosphate solutions, the addition of fluoride to the solution resulted in a (about) four times increase in hardness of dental enamel compared to similar solutions excluding fluoride.

Another, optional, ion which may be present in the supersaturated solution is zinc, in the range of from 0 to about 1 mM, such as 0 to 0.5 mM, preferably in the range of from 0 to 0.1 mM. Zinc is particularly advantageous in speeding up wound healing and in decreasing the solubility of the mineral (eg. hydroxyapatite and especially octacalcium phosphate) formed. When present, the amount of zinc is preferably chosen so that up to 50 mg, more preferably around 15 mg, is administered per treatment dose.

Where zinc is to be present in the supersaturated solution, it is preferably added to component (a) although it may also be added, at lower concentrations, to component (b). Therefore, twice the concentration of zinc must be present in the calcium concentrate (a) as specified above for the supersaturated solution.

Other, known, additives may be present in the supersaturated solution such as flavoring or colouring agents, or preservatives. Mint flavouring is especially preferred where the supersaturated solution is to be used in 'normal' patients (but it can be an irritant in bone marrow transplant (BMT) or irradiation patients). Of the usual preservatives, sodium benzoate is preferred in concentrations insufficient substantially to alter the pH of the supersaturated solution, otherwise the ratio of mono:dibasic phosphates would need to be adjusted to arrive at the desired pH.

However, other ingredients which have been known in prior art calcium/phosphate solutions are preferably excluded from the formulations of the present invention. Therefore, the aqueous, supersaturated solutions described herein are most preferably substantially free from: carbon dioxide; alcohol; silicate; acetate or other organic acid salts; chelating agent; antinucleating agent; fluorophosphate; and the like.

The solutions (including concentrates; stock solutions and supersaturated solutions) described herein preferably consist essentially of calcium ions, orthophosphate ions, sodium Ions, chloride ions and, optionally, fluoride ions and/or zinc ions in the concentrations already specified, and, if desired, colouring(s), flavourlng(s) and/or preservative(s). More preferably, the solutions are substantially free from any ion or other ingredient which is not normally present in saliva.

The present invention further provides a system for preparing an oral rinse that comprises a supersaturated calcium phosphate solution, said system comprising (a) a calcium stock solution containing calcium ions in a concentration of from about 2 to about 40 mM and sodium chloride or another physiologically acceptable stabilizer in a concentration of from about 40 to about 400 mM; (b) a phosphate stock solution separated from said calcium stock solutions, said phosphate stock solution containing phosphate ions in a concentration of from about 0.5 to about 32 mM; and sodium chloride or another physiologically acceptable stabilizer in a concentration of about 40 to about 400 mM; and (c) means for combining said calcium stock solution and said phosphate stock solution shortly before use thereof to form a supersaturated solution of calcium phosphate.

A preferred system is one wherein the pH of said stock solutions is maintained such that the pH of the supersaturated solution is in the range from about 5.0 to about 8.0. Other preferred features of the system will be appreciated from the foregoing description.

The present invention therefore still further provides a method of preparing a supersaturated calcium phosphate solution for use as an oral rinse, the solution comprising:

calcium in a concentration of from about 2 to about 40 mM;

phosphate in a concentration of from about 0.5 to about 32 mM;

sodium in a concentration of from 0 to about 0.5M;

chloride in a concentration of from 0 to about 0.5M, which method comprises (a) preparing a calcium stock solution comprising from about 4 to about 80 mM calcium ions and from about 40 to about 400 mM sodium chloride; (b) separately preparing a phosphate stock solution comprising from about 1 to about 64 mM phosphates and from about 40 to about 400 mM sodium chloride, and (c) mixing said stock solutions (a) and (b).

A preferred method is one wherein said calcium stock solution (a) is prepared by diluting a calcium concentrate with sufficient water to form said calcium stock solution; and said phosphate stock solution (b) is prepared by diluting a phosphate concentrate to form said phosphate stock solution.

Therefore, the components (a) and (b) (stock solutions) to be mixed to form the supersaturated solutions according to this invention are preferably provided as two respective concentrates (ie. each to be separately mixed with water to form the respective stock solutions prior to being mixed together to form the final, supersaturated solution or mouthwash).

For example, an optionally flavoured and coloured calcium concentrate may be provided in a container (such as a 25 ml container) which is packaged together with an optionally flavoured and coloured phosphate concentrate provided in another 25 ml container, together with instructions for dilution with, preferably, distilled water.

Therefore, the present invention further provides a formulation comprising:

(a) a calcium concentrate which itself comprises an aqueous solution of calcium ions in the range of from about 8 to about 2120 mM, such as 10 to 2080 mM, preferably 25 to 1300 mM, for example 360 mM, and 0M to 6.5M sodium chloride or equivalent stabiliser as described above, for example about 3.7M; and, associated therewith but separate therefrom (b) a phosphate concentrate which itself comprises an aqueous solution of phosphate ions in the range of from about 2 to about 1440 mM, such as 4 to 1300 mM, preferably 20 to 780 mM, for example 225 mM; and a stabilising amount of a physiologically-acceptable stabiliser such as an alkalimetal or ammonium halide such as from 0M to 6.5M sodium chloride, for example, 3.71M NaCl;

whereby, on diluting each concentrate with water in a range of ratios of from 1:1 to 1:64, preferably about 1:4 to 1:64 such as about 1:40 (concentrate:water), for example, 1:37 and thereafter mixing the two stock solutions thereby formed in a range of ratios of from 3:7 to 7:3, preferably 4:6 to 6:4, more preferably about 1:1 (calcium stock solution (a):phosphate stock solution (b)), a supersaturated solution is formed which is suitable for use as a mouthwash or dental rinse.

The calcium concentrate preferably contains sodium (ions) in the range specified above for NaCl in concentrate (a), and chloride in a range of from 0 to about 10.7M, for example 4.43M. The phosphate concentrate preferably contains chloride in the ranges given above for NaCl in concentrate (b); and sodium (ions) in the range of from 0 to about 9.38M, preferably 0.05 to 11.4M. such as 0 to 9.5M, for example 4.11 M. Zinc may be present in the calcium concentrate in the range of from 0 to about 640 mM, preferably 0 to 260 mM, such as 0 to 65 mM, for example, 1.9 mM. Fluoride may be present in the phosphate concentrate in the range of from 0 to about 500 mM, preferably 0 to 32 mM, such as 0 to 65 mM, for example 19 mM.

Optionally, colouring(s), flavouring(s) and/or preservatives(s) may also be present, as hereinbefore described.

The package preferably contains patient instructions (i) separately to mix the contents of each of the above-mentioned 25.0 ml containers with 925 ml of water (for a final volume of 950 ml [one U.S. quart]) or 13.2 ml volumes of concentrate to be diluted to form 0.5 l stock solution; (ii) then to mix at least 8 ml of each preferably in a ratio 1:1 but no less 30% calcium stock solution and no more than 70% calcium stock solution; and (iii) how to use these final, diluted, supersaturated solutions as a mouthwash or rinse for the oral cavity.

However, more preferably, the stock solutions (components (a) and (b)) are provided ready-made so that the patient or medic who is to administer the supersaturated solution only has to mix the two components to form the supersaturated solution, thereby avoid the dilution step. Conveniently, therefore, the stock solutions (a) and (b) are provided in separate, unit dose containers such as sterilised, hermetically-sealed 15 ml containers such as those available from Rommel A.G. (Stuttgart, Germany).

Very conveniently, packages may contain multiples of thirty doses with instructions for an appropriate treatment programme as herein described. For example, for OTC use, a pack may contain thirty doses as a month's daily treatment, or for clinical use such a pack may comprise a week's treatment. Alternatively, for the clinic, a pack may provide 120 doses comprising a month's treatment, depending upon the treatment programme to be followed.

Dental caries is an ubiquitous problem, particularly in elderly patients. The predominant forms of dental caries in elderly patients are root surface and recurrent carious lesions. The supersaturated solutions of the present invention have been found to have a particularly beneficial effect when used as part of a multi-component preventative treatment programme. This treatment programme aims simultaneously to increase tooth resistance, decrease the acid attack rate and enhance the intra-oral physiological maintenance processes. For example, the supersaturated solutions are preferably used in conjunction with treatment components selected from:

A. Oral hygiene: selected from flossing, standardised tooth brushing with fluoride toothpaste and cleaning of tooth surfaces with cotton swabs. Daily use of fluoride toothpaste is to maintain the fluoride levels obtained from step B below;

B. Topical fluoride applications: for example, self-administration of fluoride gel by means of custom-made trays of soft plastic (such as Mouthguard(R) material) e.g. neutral sodium fluoride gel containing ½–1% F. The fluoride application is preferably followed by the mouth being thoroughly rinsed with water to remove residual gel and prevent swallowing of fluoride; and C. Salivary gland stimulation: for example, by a non-sweetened gum for patients with xerostomia to stimulate salivary secretion.

It is especially preferred that such a preventative treatment programme should be followed before restorative procedures are undertaken in highly caries-susceptible patients. The remineralisation of some lesiorns will facilitate preparation procedures by strengthening the tissues. Also, the sensitivity of the teeth is decreased as the lesion rehardens and exposed dentinal canals close. Furthermore, it is desirable to improve the chemistry of sound tooth surfaces before major reconstructive or restorative work is begun especially since many remineralised lesions may not need to be restored, unless the patient requests restoration for aesthetic reasons.

Treatment using the supersaturated solutions in conduction with component B has been found to be especially beneficial, particularly in cancer patients. Cancer, in all its forms, is highly prevalent in present-day society, and many of the treatments associated with the various forms exhibit severe side-effects. For example, of the one million people in the United States who develop cancer annually, over 400,000 individuals suffer oral complications from their cancer therapies. Additionally, there are 25,000 individuals per year who develop leukaemia. Unfortunately, most cancer treatments affect normal tissues as well as diseased cells. As treatments become more intensive and more successful, their effects on 'normal' tissues have increased, and the oral cavity is frequently the site of severe side-effects.

The oral complications of cancer therapy are, at minimum, painful and, at their most severe, life threatening. These oral side-effects (particularly in patients undergoing chemotherapy and radiation therapy for head and neck cancer including Hodgkins disease and lymphomas) include mucositis, xerostomia, osteoradionecrosis, candidiasis and secondary infections such as herpes. Chemotherapeutic drugs also cause a variety of symptoms which may discourage eating, such as stomatitis, sore throat, change in taste sensation, stomach cramping, feeling of fullness, nausea, vomiting or diarrhoea. Malnutrition is, therefore, a common consequence of the oral complications. Other side effects include monoliasis, dysphagia, tooth hypersensitivity and rampant dental caries.

For example, bone marrow transplantation (BMT) has been found to be successful in the treatment of leukaemia, lymphoma and some solid mass tumours. Prior to a bone marrow transplant, intensive chemotherapy and total body irradiation (for allogenic BMT patients) is administered to the patient in an effort to destroy all cancer cells, The dosages must be so high that the bone marrow is destroyed, leaving the patient wholly dependent on supportive care for defence against infection until the new marrow engrafts and starts to function.

This intensive treatment places the BMT patient in need of dental intervention, since it depresses the patient's immune system. The majority of BMT patients who die do so as a result of an infection. Reverse isolation and prophylactic antibiotics are effective in preventing microbial infections except or those infections originating in the mouth. Thus, microorganisms can enter the bloodstream through ulcerations of the oral mucosa, resulting in septicemia and, in many cases, death. Studies have shown that 25% of the deaths from infections were of oral origin (as evidenced by, for example, Research Report on Leukaemia, prepared by the Office of Cancer Communications, National Cancer Institute, NIH Publication No. 88–329, 1988; and Epstein, J. B. in Infection prevention in bone marrow transplantation and radiation patients, NCI Monogr. 9 73–85, 1990).

Mucositis is therefore a common consequence not only of (high dose) radiation therapy but also in patients undergoing bone marrow transplantation. This painful condition appears three days post-induction therapy and usually continues until engraftment occurs. The pain is often so great that patients cannot eat and require high-dose morphine. This further debilitates the patient so that total parenteral nutrition is necessary to maintain nutritional levels. Mucositis is caused by non-specific inhibitory effects of the chemotherapeutic agent and radiation on mitosis of the rapidly-dividing basal epithelial cells. Atrophic changes and, eventually, ulceration are a result of this reduction in the renewal rate of basal epithelial cells. The loss of integrity of the epithelium provides a portal for the entry of oral micro-organisms at the time of maximum myelosuppression (the nadir). Oral flora have been found to be the most frequent source of sepsis in granulocytopaenic cancer patients. (NIH, ibid). Non-keratinized mucosa is more vulnerable to chemotherapeutic agents than keratinized mucosa; thus, the highly vascular lining of the floor of the mouth is a common site of entry for oral flora.

Additionally, degenerative and vascular changes in the submucosa, xerostomia and reactivation of latent viruses directly affect the epithelium. Local irritants such as ill-fitting dental appliances, cracked or rough restorations may further compromise the oral mucosa.

Although chlorhexidine has been shown to be useful in the prevention of bacterial and fungal infection, there are no consistent findings in the value of chlorhexidine in reducing mucositis in cancer patients. It probably works on the secondary microbial initiation of already-affected tissue, The problem with its use is that, once mucositis starts, the alcohol content of chlorhexidine preparations makes it difficult for the patient to use even at one-half strength. It is difficult to force the patients who are experiencing severe pain and who are already on morphine to use something that increases their pain.

Many of these side-effects can be minimised with a rigorous preventative regime. In conjunction with oral preventative care, chemical enhancement of the oral environment is essential to maintain the mucosal barrier intact. It has now surprisingly been found that chemical enhancement with the supersaturated solution of the present invention, preferably in conjunction with a multi-component treatment programme such as described above, is effective in decreasing mucositis and increasing survival and recovery. The present supersaturated solutions are effective in treating or preventing both the soft tissue and hard tissue problems or side effects mentioned above.

The supersaturated solutions of the present invention are therefore useful in the treatment or prevention of any disease, patient or condition which requires (a) remineralisation or maturation of oral hard tissue (since these solutions substantially enhance the natural, ongoing remineralisation process); and (b) anti-inflammatory, including anti-mucositis, and anti-infective, including anti-septicaemic, treatment of periodontal, soft tissue. The soft tissue effects of these solutions are particularly unexpected and include positive effects on the gums, soft and hard palates, tongue and mouth floor. Inflammation, ulceration, erythema and eruptions of the mucous membrane may all be treated or prevented with these supersaturated solutions.

It is therefore visualised that the following patient groups will benefit from the use of the supersaturated solutions according to the invention:

Oncology patients undergoing radiation therapy and/or chemotherapy both during treatment and after treatment for as long as salivary function is impaired (months to years);

Bone marrow transplant patients who often develop fatal infections in the oral cavity during and after treatment. The supersaturated calcium/phosphate mouthwash decreases mucositis and increases survival and recovery, sparing the patient pain and discomfort and decreasing hospital stay. In patients suffering from graft versus host disease, the changes to the salivary glands and oral mucosa can last for years and are very painful;

Patients suffering from medical conditions in which salivary secretion is reduced or absent (xerostomia). Specific examples include Sjøgren's syndrome, various connective tissue degenerative diseases, and congenital absence of salivary glands;

Patients with decreased salivary functions resulting from the administration of various medications, which as a side-reaction causes impairment of salivary function (psychiatric conditions, high blood pressure, 'dry-mouth' reactions to medicines etc.);

AIDS patients—to manage their severe mucositis and monoiliasis which occur in advanced stages of the disease;

Patients with high susceptibility to dental caries without specific systemic disease;

Patients with inflammatory and/or ulcerative lesions in the oral cavity—either acute, chronic or recurrent; and Any other patient, including patients with sensitive teeth, and those who wish to strengthen the teeth against dental caries and promote better oral health—by combining a fluoride treatment with the supersaturated solution mouthwash.

For remineralising use, the supersaturated solutions should be used at least twice and up to ten times per day at a time when no food or drink is to be taken for at least 30 minutes after rinsing. If in combination with fluoride gel, the supersaturated solution is to be used after the fluoride treatment. In use, the preferred supersaturated solutions of this invention are believed to form, in the oral cavity with saliva when present, a mixture having 4.7–5 mM calcium; and 3–3.3 mM phosphate; at pH 6.9–7.1.

Cancer or BMT patients may require around five treatments per day. In cases of severe mucositis, the supersaturated solutions may be used as often as twelve times per day. Usually from 15 to 40 ml of the final, supersaturated solution is required per treatment comprising two-part rinsing. For example, in the case of a 20 ml treatment, the patient rinses first with about 10 ml of the supersaturated solution for about one minute, expectorates, and then repeats this procedure.

Remineralisation following the preventative treatment program mentioned before may be complete in 'normal' patients after approximately 2 weeks of twice-daily treatments followed by about one week of once-daily treatments; however, treatment may be continued thereafter. Cancer or BMT patients may need to continue treatment indefinitely or at least until resumption of normal salivary function after which treatment would follow the pattern for 'normal' patients.

Therefore, the present invention yet further provides a method of (a) remineralizing teeth; (b) preventing or relieving mucositis in subjects in need of such treatment; and (c) preventing oral cavity infection in a patient with an impaired immune system, which method comprises periodically rinsing the oral cavity with a supersaturated solution as described hereinbefore.

EXAMPLES

The present invention will now be illustrated with reference to the following examples.

Example 1

Saliva Substitute Formulation

The following formulation is suitable for use in patients/individuals having a decreased salivary output/excretion (i.e. to moisten and lubricate the oral cavity and to act as a salivary substitute or replacement solution).

The saliva substitute is comprised of two separate concentrate solutions each of which is diluted with water and stored separately. Approximately equal volumes of the two solutions are mixed just prior to introduction into the oral cavity. The two solutions are:

A. A fresh mint-flavoured calcium concentrate; and

B. A fresh mint-flavoured phosphate concentrate, made up as follows:

| A. Calcium concentrate | |
|---|---|
| Calcium Chloride Dihydrate, USP | 52.9 g/l (380mM) |
| Sodium Chloride, USP | 217 g/l (3.71M) |
| Sodium Benzoate, USP | 1.0 gm/l |
| Fresh Mint Colouring | 1.5 ml/l |
| Fresh Mint Flavouring | 2.0 ml/l |
| Water for Injection | q.s. to 1000 ml |

| B. Phosphate concentrate | |
|---|---|
| Disodium Phosphate, USP | 24.1 g/l (170mM) |
| Monosodium Phosphate Monohydrate, USP | 7.6 g/l (55.1mM) |
| Sodium Chloride, USP | 217 g/l (3.71M) |
| Sodium Benzoate, USP | 1 g/l |
| Fresh Mint Flavouring | 2.0 ml |
| Fresh Mint Colouring | 1.5 ml |
| Water for Injection | q.s. to 1000 ml |

Each of these two concentrates is filled in a separate 25.0 ml container comprising high density polyethylene. Each container is sealed with a tamper-evident shrink film and placed in a cardboard container. The package and/or container(s) is/are labelled with the following directions. Remove the protective shrink film and cap. The entire contents of this container is to be mixed with one U.S. quart (925 ml) of water prior to use. A measuring cup (included in the package) should be used to mix together equal volumes of the diluted calcium solution (12.5 ml) and diluted phosphate solution (12.5 ml). Immediately after mixing, one half of the contents of the measuring cup should be rinsed in the mouth for 1 minute and this repeated with the remaining contents of the measuring cup. For best results it is recommended that the following rinsing schedule be followed:

| Weeks 1–2 | Rinse mouth twice per day (morning and evening) for 2 minutes |
|---|---|
| Weeks 4–6 | Rinse mouth once per day (morning and or evening) for 2 minutes. |
| Thereafter- | Rinse mouth twice per week for 2 minutes. |

The supersaturated solution may be rinsed in the mouth as often as needed to moisten and lubricate the mouth as a means of replacing decreased salivary excretions. When rinsing is completed, the solution is expectorated.

The chemical composition of these final, diluted stock solutions will be as follows.

| Calcium Stock Solution (25.0 ml concentrate + 925 ml Water) | |
|---|---|
| Calcium chloride dihydrate, USP | 1.39 g/950 ml (9.5mM) |
| Sodium Chloride, USP | 5.71 g/950 ml (97.7mM) |
| Sodium Benzoate, USP | 0.025 g/950 ml |
| Fresh Mint Colouring | 0.038 ml/950 ml |
| Fresh Mint Flavouring | 0.050 ml/950 ml |
| Water | q.s. to 950 ml |

| Phosphate Stock Solution (25.0 ml concentrate + 925 ml Water) | |
| --- | --- |
| Disodium Phosphate, USP | 0.634 g/950 ml (4.47mM) |
| Monosodium Phosphate Monohydrate, USP | 0.200 g/950 ml (1.45mM) |
| Sodium Chloride, USP | 5.71 g/950 ml (97.7mM) |
| Sodium Benzoate, USP | 0.025 g/950 ml |
| Fresh Mint Flavouring | 0.038 ml/950 ml |
| Fresh Mint Colouring | 0.050 ml/950 ml |
| Water | q.s. to 950 ml |

Example 2

Remineralising Solution

Alternatively, supersaturated solutions according to this invention may be prepared by:

| A. Calcium concentrate (1 US gallon) | |
| --- | --- |
| Calcium chloride dihydrate | 200 g (360mM) |
| Sodium chloride | 821 g (3.71M) |
| Sterile water | q.s. ad 3785 ml |

| B. Phosphate concentrate (1 US gallon) | |
| --- | --- |
| Monobasic sodium phosphate ($NaH_2PO_4$) | 25 g (55.1mM) |
| Dibasic sodium phosphate ($Na_2HPO_4 \cdot 7H_2O$) | 172 g (170mM) |
| Sodium chloride | 821 g (3.71 m) |
| Sterile water | q.s. ad 3785 ml |

In each case, the salts-are sifted together in a 4000 ml stainless steel container. They are then added gradually to 2000 ml water for irrigation in a 4000 ml Erlenmeyer flask. Once the reaction has subsided, sufficient water is added to make 1 US gallon (3785 ml). The concentrate is then passed through a large 40 cm filter paper into a plastic gallon. Thereafter, it is packaged in 25 ml volumes into 30 ml plastic squeeze containers.

To make the remineralising solution, 25 ml of each concentrate is separately diluted with one US quart (925 ml) of tap water, to form stock solutions. 30 ml of each stock solution are mixed together to form the remineralising solution.

Example 3

Remineralisation of Carious Lesions in Elderly Patients

Two studies were carried out independently of each other.

Study 1

A total of 171 patients were studied. The ages of the patients ranged from 2½ to 76 years old. Data on 30 patients, 45 years old and older, are included in this example. The patients were selected because of existing extensive caries and/or documented histories of high caries susceptibility over several years.

On the basis of general health status, the 30 participating subjects were divided into two groups. The 18 patients included in Group A suffered from various diagnosed illnesses including diabetes, high blood pressure, Parkinson's disease and cancer, and received various types of medications. In contrast, Group B consisted of 12 healthy individuals who were not on any medication. This example covers only the first 4 years of treatment.

Study 2

More than 500 patients of all ages participated in this study, but this example includes only the findings on 94 patients aged 45 years and older.

In both studies, the preventative procedures were explained and demonstrated to each patient either individually or in small groups, and written instructions were also provided. Briefly stated, the preventative procedures were as follows:

1. Oral hygiene: Flossing, standardised tooth brushing with fluoride toothpaste, ana cleaning of tooth surfaces with cotton swabs.

2. Topical fluoride applications: Self-administration of fluoride gel by means of custom-made trays of soft plastic (Mouthguard® material). Neutral sodium fluoride gel containing 1% F was prescribed for most patients. In some instances, gel with only half the F concentration was used. The initial home treatment schedule consisted of two 5-minute applications per day for 2 weeks followed by singel daily applications for an additional 2 weeks. Following each treatment, the mouth was to be thoroughly rinsed with water to remove residual gel and prevent swallowing of fluoride. For some patients, a limited number of booster treatments were prescribed on an individual basis at different times during the period of study.

3. Remineralising mouthwash: The composition of the remineralising supersaturated solution at pH 7.0 (±0.2) was 4.74 mM Ca, 2.96 mM $PO_4$, 0.107M Na, 0.103M Cl and 0.25 mM fluoride.

The remineralising solution was prepared substantially in accordance with Example 2 but with the addition of 19 mM fluoride in the Phosphate concentrate; resulting in 0.5 mM fluoride in the phosphate stock solution (hence 0.25 mM in the supersaturated solution). The two stock solutions (which were stored separately and mixed as described in Examples 1 and 2 immediately prior to use) comprised:

| Calcium stock solution (a) | |
| --- | --- |
| $Na^+$ | 0.098M |
| $Cl^-$ | 0.117M |
| $Ca^{++}$ | 9.47mM |
| pH | 4–6 |

| Phosphate stock solution (b) | |
| --- | --- |
| $Na^+$ | 0.108M |
| $Cl^-$ | 0.098M |
| $H_xPO_4$ | 5.92mM (4.47mM dibasic + 1.45mM monobasic) |
| F | 0.5mM |
| pH | 7–7.3 |

A 2-minute rinse was prescribed after each topical fluoride application. When the fluoride gel treatment was completed, patients with limited salivary secretion were asked to continue using the rinse solutions twice a day after toothbrushing.

4. Salivary gland stimulation: A non-sweetened gum was prepared and prescribed for patients with xerostomia to stimulate salivary secretion.

The two studies described differ in several respects. In study 1, the patients were not under close observation after the initial 46 weeks, when the preventative treatment procedures had been completed. Some patients were only recalled at 6- to 12-month intervals for re-examination while others were seen at shorter intervals for the rendering of restorative or periodontal treatment. At all appointments, the maintenance of good oral hygiene was emphasized. Additional supplies of rinse solution were made available to all participants during the first year, but subsequently fluoride gel and remineralizing solution were given primarily to patients with impaired salivary function. Thus, not all of the participants followed the same routine after the original preventative treatment. In contrast, the participants in study 2 were monitored carefully and given remineralising solutions as requested and fluoride as deemed necessary. Patients with apparently stable oral health conditions were recalled less Frequently than the oncology patients who were at greater risk of losing their teeth.

The findings in both studies confirm the ability of the treatment system to remineralize active carious lesions. The greatest success was obtained with root surface lesions.

The incidence of new carious lesions in both groups dropped close to zero. The fluoride levels of enamel, dentin and cementum increased markedly, to a level where the crystallites apparently become more resistant to demineralisation. The fact that the caries resistance persists over several years adds further credence to this explanation. Some of these patients have had no cavity now for up to 16 years, and several for up to 10 years. The benefit is clearly not a temporary phenomenon, but represents a permanent increase in tooth resistance to caries Example 4

Clinical Studies on BMT Patients—Soft Tissue Effects

In order to stimulate salivary secretion, BMT patients were supplied with inert chewing gum. They were also given individual instructions on proper oral hygiene, as well as nutritional counselling.

In order to minimise the dangers of septicemia, a rigorous oral management regimen was instituted. This example presents the findings from a retrospective study comparing patients who received an intensive oral preventative regimen (including the solution of the present invention) during hospitalisation with those who did not receive such treatment.

The bone marrow transplant protocols were the same for all patients. The treatment regimens for autologous bone marrow transplant patients were:

| | | |
|---|---|---|
| Cytoxan | 12,000 mg/m$^2$ | 4 times per day |
| Carboplatin | 1,600 mg/m$^2$ | 4 times per day |
| VP16 (Etoposide) | 1,600 mg | 4 times per day |

TABLE 1A

Study 1: Remineralization of active carious lesions

| | | Patient Population | | |
|---|---|---|---|---|
| | | | Mean | |
| Group* | No. | Age | DMFT | No. of Teeth Present |
| A. | 12 | 50 | 25 | 22 |
| B. | 18 | 58 | 27 | 21 |

| | Pre-treatment Active Lesions | | Post-treatment Remineralized Lesions Year | | | | | | | |
|---|---|---|---|---|---|---|---|---|---|---|
| | No. | % | No. | % | No. | % | No. | % | No. | % |
| Totals | 206 | 100 | 156 | 76 | 130 | 63 | 124 | 60 | 116 | 58 |

*A - Patients without diagnosed medical problems
B - Patients with medical problems

TABLE 1B

Study 2: Remineralization of active carious lesions

| | Pre-treatment: Types and No. of Lesions | | | | Post-treatment: Remineralized Surfaces | | | |
|---|---|---|---|---|---|---|---|---|
| | No. of | No. of | Root Caries | Coronal Caries | Root Caries | | Coronal Caries | |
| Group | Teeth | Carious Teeth | No. of Surfaces | No. of Surfaces | No. of Surfaces | % of Surfaces | No. of Surfaces | % of Surfaces |
| Radiation Therapy | 1002 | 448 | 490 | 277 | 354 | 72* | 144 | 52 |
| Xerostomia | 182 | 87 | 139 | 18 | 125 | 90 | 13 | 72 |
| Sjögren's Syndrome | 210 | 116 | 166 | 50 | 144 | 87 | 26 | 52 |
| High Caries Susceptibility | 308 | 114 | 149 | 23 | 102 | 68 | 5 | 22 |
| TOTALS | 1702 | 765 | 944 | 368 | 725 | 77 | 188 | 51 |

*In 23 patients of the Radiation Therapy group, 100% of the 243 carious surfaces were remineralized.

For allogenic bone marrow transplant patients, the treatment regimens were:

| | |
|---|---|
| Cytoxan | 60 mg/kg/day × 2 |
| Total Body Irradiation | 300 Rads/QDX given twice per day |

All patients received prevention education and comprehensive dental care before therapy. All patients completed their dental treatment before going in for therapy. Before therapy began, the patients maintained a daily regimen of using custom fluoride trays with 2% sodium fluoride. (Fluoride gel is placed in the custom tray and inserted in the mouth for approximately five minutes twice per day.) Chlorhexidine was used as long as the patient could tolerate it—usually until the onset of mucositis.

All BMT recipients were referred from the Hematology-Oncology Division of New England Medical Center, Boston, Mass., U.S.A Group 1 19 BMT patients who had received comprehensive dental care before entering therapy, custom fluoride trays with 2% sodium fluoride and Peridex (Registered Trademark) rinse b.i.d. were administered with no follow-up dental care. Saline and peroxide rinses, 2-2-2 solutions, Peridex (Registered Trademark) and Nystatin (Registered Trademark) were used. Prophylactic antibiotics and acyclovir were used.

Group 2 39 BMT patients who had received comprehensive dental care before entering therapy and throughout their hospital stay, custom fluoride trays with 2% sodium fluoride and Peridex (Registered Trademark) rinse b.i.d. and supersaturated calcium/phosphate remineralising rinses according to Example 3. (2 US fl. oz. (59 ml) used 4–5 times per day). Peridex (Registered Trademark) and Nystatin (Registered Trademark) were used. Prophylactic antibiotics and acyclovir were used.

TABLE 2A

PATIENT POPULATION BY DIAGNOSIS

| | Dental Preventative Treatment? | |
|---|---|---|
| | NO<br>N = 19 | YES<br>N = 39 |
| LEUKAEMIA | 8 | 12 |
| HODGKINS DISEASE | 4 | 10 |
| LYMPHOMA | 4 | 14 |
| OTHER | 3 | 3 |

The records of 58 bone marrow transplant patients (19 allogenic; 39 autologous) ages 20–57 were reviewed for length of stay (post transplantation), days of neutropaenia, days of morphine, days of fever, days of infection, total parenteral nutrition (TPN) and duration of mucositis.

TABLE 2B

RESULTS FOR All BMT PATIENTS

| | Dental Preventative Treatment? | |
|---|---|---|
| | NO<br>N = 19 | YES<br>N = 39 |
| LENGTH OF STAY POST TRANSPLANTATION | 30.2 | 28.7 |
| DAYS OF NEUTROPAENIA (White blood cell count below 500) | 16.0 | 10.9 |

TABLE 2B-continued

RESULTS FOR All BMT PATIENTS

| | Dental Preventative Treatment? | |
|---|---|---|
| | NO<br>N = 19 | YES<br>N = 39 |
| DAYSOFFEVER | 7.70 | 7.05 |
| DAYS OF INFECTION | 8.6 | 4.5 |
| DAYS OF MUCOSITIS | 13.3 | 9.5 |
| DAYS OF MORPHINE | 5.15 | 3.38 |

When allogenic and autologous transplantations were separated, allogenic transplantation patients had more difficulty in all the measures than the autologous ones. All the cases which did not have the dental preventative treatment developed severe and prolonged mucositis; in one of these cases, a systemic infection originating in the mouth led to the patient's death. The allogenic patients who had the dental preventive treatment had very mild mucositis except for those who developed graft vs. host disease and died.

The results of this retrospective study demonstrate that a preventative regimen using a supersaturated calcium/phosphate solution of this invention can protect the oral mucosa, treat and prevent mucositis and reduce the severity of infection and length of stay in reverse isolation.

Examples 5 & 6

Zinc-containing Mouthrinses

According to the methods of Examples 1 and 2, the following stock solutions were prepared from the following concentrates, and mixed (component (a):component (b)= 1:1) to form a supersaturated solution having pH~7 containing (5) zinc but substantially no fluoride; and (6) fluoride and zinc:

| EXAMPLE 5 | | | EXAMPLE 6 | |
|---|---|---|---|---|
| Stock | Concentrate | | Concentrate | Stock |
| | | Component (a) | | |
| 0.1166M | 4.43M | $Cl^-$ | 4.43M | 0.1166M |
| 0.0977M | 3.71M | $Na^+$ | 3.71M | 0.0977M |
| 9.474mM | 360mM | $Ca^{++}$ | 360mM | 9.474mM |
| 0.05mM | 1.9mM | $Zn^{++}$ | 1.9mM | 0.05mM |
| 4–6 | — | pH | — | 4–6 |
| | | Component (b) | | |
| 0.0977M | 3.71M | $Cl^-$ | 3.71M | 0.0977M |
| 0.1081M | 4.11M | $Na^+$ | 4.11M | 0.1081M |
| 1.45mM | 55.1mM | $H_2PO_4^-$ | 55.1mM | 1.45mM |
| 4.47mM | 169.9mM | $HPO_4^-$ | 169.9mM | 4.47mM |
| Ø | Ø | $F^-$ | 19mM | 0.50mM |
| 7–7.3 | — | pH | — | 7–7.3 |

| Stock | Concentrate | Component (a) | Concentrate | Stock |
|---|---|---|---|---|
| 0.098M | 3.71M | NaCl | 3.71M | 0.098M |
| 9.474mM | 360mM | $CaCl_2$ | 360mM | 9.474mM |
| 0.05mM | 1.90mM | $ZnCl_2$ | 1.90mM | 0.05mM |

-continued

| EXAMPLE 5 | | Component (b) | EXAMPLE 6 | |
|---|---|---|---|---|
| 0.098M | 3.71M | NaCl | 3.71M | 0.098M |
| 1.45mM | 55.1mM | NaH$_2$PO$_4$ | 55.1mM | 1.45mM |
| 4.47mM | 169.9mM | Na$_2$HPO$_4$ | 169.9mM | 4.47mM |
| Ø | Ø | NaF | 19mM | 0.5mM |

Examples 7–9
Mouthrinses Having Non-Neutral pH

According to the methods of Examples 1 and 2, the following stock solutions were prepared from the following concentrates, and mixed (component (a):component (b)= 1:1) to form a supersaturated solution having non-neutral pH:

Example 7
Supersaturated Solution pH~6.5

| Stock | | Concentrate |
|---|---|---|
| | Component (a) | |
| 0.1333M | Cl$^-$ | 5.07M |
| 0.0977M | Na$^+$ | 3.71M |
| 17.8mM | Ca$^{++}$ | 676.4mM |
| 4–6 | pH | — |
| | Component (b) | |
| 0.0977M | Cl$^-$ | 3.71M |
| 0.1134M | Na$^+$ | 4.31M |
| 6.68mM | H$_2$PO$_4^-$ | 253.8mM |
| 4.53mM | HPO$_4^=$ | 172.1mM |
| 0.50mM | F$^-$ | 19mM |
| 6.6–6.7 | pH | – |

In this example, ions were supplied as follows:

| Stock | | Concentrate |
|---|---|---|
| | Component (a) | |
| 0.098M | NaCl | 3.71M |
| 17.8mM | CaCl$_2$ | 676.4mM |
| Ø | ZnCl$_2$ | Ø |
| | Component (b) | |
| 0.098M | NaCl | 3.71M |
| 6.68mM | NaH$_2$PO$_4$ | 253.8mM |
| 4.53mM | Na$_2$HPO$_4$ | 172.1mM |
| 0.50mM | NaF | 19.00mM |

| EXAMPLE 8 Saturated Solution pH ~7.5 | | EXAMPLE 9 Supersaturated Solution pH ~6.0 | |
|---|---|---|---|
| Stock | Concentrate | Concentrate | Stock |
| | Component (a) | | |
| 0.1099M | 4.17M | Cl$^-$ 6.44M | 0.17M |
| 0.0977M | 3.71M | Na$^+$ 3.71M | 0.098M |
| 6.08mM | 231mM | Ca$^{++}$ 1364mM | 35.9mM |
| 0.05mM | 1.9mM | Zn$^{++}$ 3.8mM | 0.10mM |
| 4–6 | — | pH — | 4–6 |

| EXAMPLE 8 Saturated Solution pH ~7.5 | | EXAMPLE 9 Supersaturated Solution pH ~6.0 | |
|---|---|---|---|
| Stock | Concentrate | Concentrate | Stock |
| | Component (b) | | |
| 0.0977M | 3.71M | Cl$^-$ 3.71M | 0.0977M |
| 0.105M | 3.99M | Na$^+$ 4.72M | 0.1241M |
| 0.319mM | 12.12mM | H$_2$PO$_4^-$ 699mM | 18.4mM |
| 3.48mM | 132.2mM | HPO$_4^=$ 152.4mM | 4.01mM |
| Ø | Ø | F$^-$ 19mM | 0.50mM |
| 7.7–7.9 | — | pH — | 6–6.2 |

| Stock | Concentrate | | Concentrate | Stock |
|---|---|---|---|---|
| | | Component (a) | | |
| 0.098M | 3.71M | NaCl | 3.71M | 0.098M |
| 6.08mM | 231.0mM | CaCl$_2$ | 1364mM | 35.9mM |
| 0.05mM | 1.90mM | ZnCl$_2$ | 3.80mM | 0.1mM |
| | | Component (b) | | |
| 0.098M | 3.71M | NaCl | 3.71M | 0.098M |
| 0.319mM | 12.12mM | NaH$_2$PO$_4$ | 699mM | 18.4mM |
| 3.48mM | 132.2mM | Na$_2$HPO$_4$ | 152.4mM | 4.01mM |
| Ø | Ø | NaF | 19mM | 0.5mM |

Example 10

The supersaturated solution formed in accordance with Example 7 could alternatively be formulated from the calcium (component (a)) stock and concentrate solutions described therein, but replacing the phosphate (component (b)) stock and concentrate solutions with:

| Stock | Component (b) | Concentrate |
|---|---|---|
| 0.098M | NaCl | 3.71M |
| 6.68mM | H$_3$PO$_4$ | 253.5mM |
| 4.53mM | Na$_3$PO$_4$ | 172.1mM |
| 0.50mM | NaF | 19mM |
| 6.6–6.7 | pH | — |

Example 11

The following concentrates were prepared in accordance with the method of Example 1

| | A | B |
|---|---|---|
| Calcium chloride dihydrate | 52.9 g | 55.7 g |
| Sodium chloride | 217.0 g | 228.3 g |
| Monosodium phosphate dihydrate | 8.6 g | 9.1 g |
| Disodium phosphate dodecahydrate | 60.8 g | 64.0 g |
| Sodium chloride | 217.0 g | 228.3 g |

In the case of solution A, the dilution from concentrate to stock solution was 38-fold as in Example 1, whereas in the case of solution B, the dilution from concentrate to stock solution was 40-fold.

What is claimed is:
1. A formulation which is effective for use as a dental rinse or mouthwash and which formulation comprises:

(a) a calcium component (calcium stock solution) which itself comprises an aqueous solution of calcium ions and stabilizing agent; and, associated therewith but separate therefrom, (b) a phosphate component (phosphate stock solution) which itself comprises an aqueous solution of phosphate ions and stabilizing agent;

wherein the calcium and phosphate ions are present in amount sufficient to form, on mixing and prior to use, a supersaturated solution thereof having a pH of from about 5 to about 8 and substantially free from carbon dioxide, alcohol, silicate, acetate or other organic acid salt, chelating agent, antinucleating agent, and fluorophosphate, wherein the stabilizing agent referred to in paragraphs (a) and (b) hereof is selected from the group of one or more salts of the cations $Na^+$, $K^+$, $NH_4^+$, $Mg^{++}$ and $Sr^{++}$ and the anions $Cl^-$, $CO_3^-$, $HCO_3^-$, and $NO_3^-$, and wherein the amount of stabilizing agent in each component is sufficient to enable the calcium and phosphate ions to remain for at least 1 minute at body temperature in supersaturated solution once components (a) and (b) are mixed.

2. A formulation according to claim 1 wherein the concentration of calcium ions in the stock solution is from about 4 to about 80 mM and the concentration of the stabilizer of (a) is from about 40 to about 400 mM and the phospate component comprises (ortho)phosphate ions having a concentration in the range of from about 1 to about 64 mM and the concentration of the stabilizer of (b) is from about 400 mM.

3. A formulation according to claim 1, wherein the calcium component (a) is substantially free from phosphate ions and the phosphate component (b) is substantially free from calcium ions.

4. A formulation according to claim 1, wherein the supersaturated solution remains so at room temperature or ambient temperature for at least about one hour.

5. A formulation according to claim 1, wherein the supersaturated solution has a pH of about neutral.

6. A formulation according to claim 2, wherein the concentration of calcium ions in the calcium stock solution is in the range of from about 5 to 20 mM.

7. A formulation according to claim 6, wherein the concentration of phosphate ions (total (ortho)phosphate) in the phosphate stock solution is in the range of from about 4 to about 8 mM.

8. A formulation according to claim 6, wherein component (b) comprises a mixture of monobasic phosphate with dibasic phosphate in a ratio in the order of about 1:2–1:8.

9. A formulation according to claim 1, wherein the stabilising agent of each of components (a) and (b) comprises sodium chloride.

10. A formulation according to claim 1, wherein said component (a) and (b) comprises both sodium ions and chloride ions, each independently in a concentration of up to about 0.5M.

11. A formulation according to claim 2, wherein component (b) further comprises fluoride ions.

12. A formulation according to claim 2, wherein component (a) further comprises zinc ions.

13. A concentrate formulation which upon dilution with water forms a solution that is effective for use as a dental rinse or mouthwash and which comprises:

(a) a calcium concentrate which itself comprises an aqueous solution of calcium ions and stabilising agent; and, associated therewith but separate therefrom, (b) A phosphate concentrate which itself comprises an aqueous solution of phosphate ions and stabilising agent;

wherein the stabilising agents referred to in paragraphs (a) and (b) hereof are selected from the group of one or more salts of cations $Na^+$, $K^+$, $NH_4^+$, $Mg^{++}$ and $Sr^{++}$ and the anions $Cl^-$, $CO_3^-$, $HCO_3^-$, and $NO_3^-$, wherein the calcium and phosphate ions and stabilising agents are present in such amounts whereby, on diluting each concentrate (a) and (b) with water and thereafter mixing the two stock solutions (a) and (b) thereby formed, there is formed a solution which is supersaturated with respect to calcium phosphates, which has a pH in the range of from about 5 to about 8, and which is substantially free from carbon dioxide, alcohol, silicate, acetate or other organic acid salt, chelating agent, antinucleating agent, and fluorophosphate, and which remains so for at least 1 minute at body temperature.

14. A concentrate formulation according to claim 13 wherein the concentration of the calcium ions in the calcium concentrate is in the range of from about 8 to about 2120 mM and and the concentration of the stabilizing agent is up to 6.5M and the concentration of the phosphate ions in the phosphate concentrate in the range of from about 2 to about 1440 mM and and the concentration of the stabilizing agent is up to 6.5 M.

15. A pack for use by or with a patient for administration to the oral cavity comprising a concentrate formulation according to claim 13 in association with instructions for diluting each concentrate (a) and (b) with water and for thereafter mixing the resulting stock solutions (a) and (b).

16. A pack for use by or with a patient for administration to the oral cavity comprising a stock solution formulation according to claim 1 in association with instructions for mixing stock solution components (a) and (b) and for thereafter using the resulting supersaturated solution as a mouthwash or rinse for the oral cavity.

17. A supersaturated solution which is effective for use as a dental rinse or mouthwash and which is prepared by mixing the calcium and phosphate stock solutions (a) and (b) according to claim 1.

18. A method for the treatment or prevention of a condition of the hard tissue of the oral cavity which method comprises the administration to a patient in need thereof of a non-toxic effective amount of a supersaturated solution according to claim 17.

19. A method of preparing a solution supersaturated with respect to calcium and phosphate(s) for use as an oral rinse, which solution comprises:

calcium ions in a concentration in the range of from about 2 to about 40 mM;

(ortho)phosphate ions in a concentration in the range of from about 0.5 to about 32 mM; and sodium ions in a concentration in the range of from 0 to about 0.5M which method comprises mixing: (a) a calcium stock solution comprising from 4 to about 80 mM calcium ions and from about 0 to about 400 mM sodium chloride; and (b) a phosphate stock solution comprising from about 1 to about 64 mM (ortho) phosphates and from about 0 to about 40 mM sodium chloride to form said supersaturated solution.

20. A formulation which is effective for use as a dental rinse or mouthwash and which formulation is a supersaturated solution of calcium phosphates that has a pH of from about 5 to about 8, that is substantially free from carbon dioxide, alcohol, silicate, acetate or other organic acid salt, chelating agent, antinucleating agent, and fluorophosphate, and that is formed by mixing:
(a) a calcium stock solution comprising an aqueous solution of calcium ions and a physiologically acceptable first stabilising agent; and
(b) a phosphate stock solution comprising an aqueous solution of phosphate ions and a physiologically acceptable second stabilising agent,
wherein each of said first and second stabilising agents is selected from the groups of one or more salts of the cations $Na^+$, $K^+$, $NH_4^+$, $Mg^{++}$ and $Sr^{++}$ and the anions $Cl^-$, $CO_3^=$, $HCO_3^-$, and $NO_3^-$, wherein the calcium ions in the calcium stock solution and the phosphate ions in the phosphate stock solution are present in amounts sufficient to form, on mixing and prior to use, a solution which is supersaturated with respect to calcium phosphate(s) and which contains enough of said first and second stabilising agents to remain supersaturated for at least one minute at body temperature.

21. The formulation of claim 20 wherein said first and second stabilising agents are sodium chloride.

22. The formulation of claim 20 wherein the formulation has a pH of about neutral.

23. The formulation of claim 20 wherein the calcium stock solution comprises about 4 to about 80 mM calcium ions and about 40 to about 400 mM of said first stabilising agent, and the phosphate stock solution comprises about 1 to about 64 mM phosphate ions, measured as (ortho)phosphate ions, and about 40 to about 400 mM of said second stabilising agent.

24. The formulation of claim 23 wherein the calcium stock solution comprises about 5 to about 20 mM calcium ions.

25. The formulation of claim 23 wherein the phosphate stock solution comprises about 4 to about 8 mM phosphate ions, measured as (ortho)phosphate ions.

26. The formulation of claim 20 wherein the phosphate stock solution comprises a mixture of monobasic phosphate and dibasic phosphate in a ratio from about 1:2 to about 1:8.

27. The formulation of claim 20 wherein said phosphate stock solution comprises fluoride ions and said calcium stock solution is substantially free of fluoride ions.

28. The formulation of claim 20 wherein said calcium stock solution comprises zinc ions and said phosphate stock solution is substantially free of zinc ions.

29. The formulation of claim 20 wherein said calcium stock solution is substantially free of phosphate ions and said phosphate stock solution is substantially free of calcium ions.

30. The formulation of claim 20 wherein said calcium stock solution is prepared by diluting with water a first concentrated aqueous solution of calcium ions and said physiologically acceptable first stabilising agent, and said phosphate stock solution is prepared by diluting with water a second concentrated aqueous solution of phosphate ions and said physiologically acceptable second stabilising agent.

31. The formulation of claim 20 wherein said first concentrated aqueous solution comprises about 8 to about 2120 mM calcium ions and up to about 6.5 M of said first stabilising agent, and the phosphate stock solution comprises about 80 to about 1440 mM phosphate ions, measured as (ortho)phosphate ions, and up to about 6.5 M of said second stabilising agent.

32. A method for the treatment or prevention of a condition of the hard tissue of the oral cavity by administering to a patient in need thereof a supersaturated solution of calcium ions and phosphate ions and which has been prepared by mixing:

(a) a calcium stock solution comprising an aqueous solution of calcium ions and a physiologically acceptable first stabilising agent; and
(b) a phosphate stock solution comprising an aqueous solution of phosphate ions and a physiologically acceptable second stabilising agent;
wherein each of said first and second stabilising agents is selected from the group of one or more salts of the cations $Na^+$, $K^+$, $NH_4^+$, $Mg^{++}$ and $Sr^{++}$ and the anions $Cl^-$, $CO_3^=$, $HCO_3^-$, and $NO_3^-$, wherein the calcium ions in the calcium stock solution and the phosphate ions in the phosphate, stock solution are present in amounts sufficient to form, on mixing and prior to use, a solution which is supersaturated with respect to calcium ions and phosphate ions, which has a pH in the range of from about 5 to about 8, which contains enough of said first and second stabilising agents to remain supersaturated for at least one minute at body temperature, and which is substantially free from carbon dioxide, alcohol, silicate, acetate or other organic acid salt, chelating agent, antinucleating agent, and fluorophosphate.

33. A pack for use by or with a patient who is in need of treatment involving remineralisation of the oral cavity, the pack comprising:
(a) a calcium stock solution or a concentrate therefor comprising an aqueous solution of calcium ions and stabilising agent;
(b) a phosphate stock solution or a concentrate therefor comprising an aqueous solution of phosphate ions and stabilising agent;
(c) instructions for mixing said stock solutions (a) and (b) to form a supersaturated solution of calcium and phosphate ions and for administering said supersaturated solution to said patient,
wherein the stabilising agents refered to in paragraphs (a) and (b) hereof are selected from the group of one or more salts of the cations $Na^+$, $K^+$, $NH_4^+$, $Mg^{++}$ and $Sr^{++}$ and the anions $Cl^-$, $CO_3^=$, $HCO_3^-$, and $NO_3^-$, wherein the calcium ions in the calcium stock solution or concentrate and the phosphate ions in the phosphate stock solution or concentrate are present in amounts sufficient to form, on mixing and prior to use, a solution which has a pH in the range from about 5 to about 8, which is supersaturated with respect to calcium and phosphate ions, which contains enough of the stabilising agents to remain supersaturated for at least 1 minute at body temperature, and which is substantially free from carbon dioxide, alcohol, silicate, acetate or other organic acid salt, chelating agent, antinucleating agent, and fluorophosphate.

34. The pack of claim 33 wherein said stabilising agents are sodium chloride.

35. The pack of claim 33 wherein the calcium stock solution comprises about 4 to about 80 mM calcium ions and about 40 to about 400 mM stabilising agent and the phosphate stock solution comprises about 1 to about 64 mM (ortho)phosphate ions and about 40 to about 400 mM stabilising agent.

36. The pack of claim 35 wherein the calcium stock solution comprises about 5 to about 32 mM calcium ions and about 80 to about 200 mM stabilising agent and the phosphate stock solution comprises about 3 to about 20 mM (ortho)phosphate ions and about 80 to about 200 mM stabilising agent.

37. The pack of claim 33 wherein said phosphate stock solution further comprises fluoride ions and said calcium stock solution is substantially free from fluoride ions.

38. The pack of claim 33 wherein said calcium stock solution comprises zinc ions and said phosphate stock solution is substantially free from zinc ions.

39. The pack of claim 33 wherein said supersaturated solution contains enough stabilising agent to remain supersaturated for up to about five minutes at body temperature.

40. The pack of claim 33 wherein said supersaturated solution contains enough stabilising agent to remain supersaturated for about three to fifteen minutes at room temperature.

41. The pack of claim 33 wherein said supersaturated solution contains enough stabilising agent to remain supersaturated for up to about one hour at room temperature.

42. The pack of claim 33 wherein said supersaturated solution contains enough stabilising agent to remain supersaturated for up to about two hours at room temperature.

43. The pack of claim 33 wherein the instructions further comprise those for using said supersaturated solution in conjunction with a topical fluoride application.

44. The pack of claim 43 wherein the topical fluoride comprises 0.5 to 1% fluoride.

45. The pack of claim 43 wherein the topical fluoride comprises 2% sodium fluoride.

46. A method according to claim 32 wherein the condition requires remineralisation or maturation of oral hard tissue.

47. A method according to claim 32 wherein the condition is selected from the group consisting of sensitive teeth and dental caries.

48. A method according to claim 32 wherein the concentrations of the calcium ions is in the range of from about 4 to about 80 mM and the concentration of stabilizer of (a) is from about 40 to about 400 mM and the phosphate component comprises (ortho)phosphate ions having a concentration in the range of from about 1 to about 64 mM and the concentration of the stabilizer of (b) is from about 40 to about 400 mM.

49. A method according to claim 32 wherein the components (a) and (b) consist essentially of calcium ions, orthophosphate ions, sodium ions, chloride ions and, optionally, fluoride and/or zinc ions, and/or colouring(s), flavouring(s) and/or preservatives, but are substantially free from any other ingredient that is not normally present in saliva.

50. A method according to claim 32 wherein the supersaturated solution remains so at room or ambient temperature for at least about one hour.

51. A method according to claim 32 wherein the supersaturated solution has a pH of about neutral.

52. A method according to claim 32 wherein the concentration of calcium ions is in the range of from about 5 to about 20 mM and the concentration of the stabilising agent (a) is from about 80 to about Z0mM and the phosphate component comprises (ortho)phosphate ions having a concentration in the range of from about 4 to about 8 mM and the stabilizing agent of (b) is from about 80 mM to about 200 mM, and wherein the supersaturated solution is substantially free from other ingredients not normally present in saliva except, optionally, fluoride and/or zinc ions, and/or colouring(s), flavouring(s), and/or preservative(s).

53. A method according to claim 32 wherein the concentration of calcium ions in the calcium stock solution is in the range of from about 5 to 20 mM.

54. A method according to claim 32 wherein the concentration of phosphate ions (total (ortho)phosphate) in the phosphate stock solution is in the range of from about 4 to about 8 mM.

55. A method according to claim 32 wherein component (b) comprises a mixture of monobasic phosphate with dibasic phosphate in a ratio on the order of about 1:2 to 1:8.

56. A method according to claim 32 wherein the stabilising agents comprise sodium chloride.

57. A method according to claim 32 wherein each component (a) and (b) comprises both sodium ions and chloride ions, each independently in an amount up to about 0.5M.

58. A method according to claim 32 wherein the concentration of calcium ions is in the range of from about 5 to about 32 mM and the concentration of the stabilizing agent is from about 80 to about 200 mM and the phosphate component comprises (ortho)phosphate ions having a concentration in the range of from about 3 to about 20 mM and the concentration of the stabilizing agent is from about 80 mM to about 200 mM, and wherein the supersaturated solution is substantially free from other ingredients not normally present in saliva except, optionally, fluoride and/or zinc ions, and/or colouring(s), flavouring(s) and/or preservatives.

59. A formulation according to claim 2 wherein the concentration of the calcium ions is from about 5 to about 20 mM, the concentration of the stabilizing agent of (a) is from about 80 to about 200 mM stabilizing agent, the concentration of the (ortho)phosphate ions is from about 4 to about 8 mM, and the concentration of the stabilizing agent of (b) is from about 80 to about 200 mM stabilizing agent, and wherein the formulation includes also flouride and/or zinc ions, and/or colouring(s) and/or flavouring(s) and/or preservative(s), and is substantially free from other ingredients not normally present in saliva.

60. A formulation according to claim 1 wherein the concentration of the calcium ions is in the range of from about 5 to about 32 mM and the concentration of the stabilizing agent of (a) is from about 80 to about 200 mM, the phosphate component comprises (ortho)phosphate ions having a concentration in the range of from about 3 to about 20 mM and the concentration of the stabilizing agent of (b) is from about 80 to about 200 mM, and wherein the formulation includes fluoride and/or zinc ions, and/or colouring(s), flavouring(s) and/or preservative, and which is substantially free from other ingredients not normally present in saliva.

61. A method according to claim 18 which includes also the administration to the patient of a topical fluoride application.

62. A method according to claim 61 wherein the topical fluoride application includes the self-administration by the patient of a fluoride gel.

63. A method according to claim 32 which includes also the administration to the patient of a topical fluoride application.

64. A method according to claim 63 wherein the topical fluoride application includes the self-administration by the patient of a fluoride gel.

* * * * *